United States Patent [19]

Millet-Genin et al.

[11] Patent Number: 5,290,563

[45] Date of Patent: Mar. 1, 1994

[54] METHOD FOR COMBINING A MIXTURE OF HETEROGENEOUS SUBSTANCES WITH LIPOSOMES

[75] Inventors: Isabelle Millet-Genin, Plaisir; Francis Puisieux, Maisons Alfort; Tran X. Thao, Chatenay Malabry; Liliane Roblot-Treupel, Thiais, all of France

[73] Assignee: Laboratoire Des Stallergenes, France

[21] Appl. No.: 797,151

[22] Filed: Nov. 26, 1991

Related U.S. Application Data

[63] Continuation of Ser. No. 556,727, Jul. 25, 1990, abandoned.

[30] Foreign Application Priority Data

Jul. 27, 1989 [FR] France .................................. 8910129

[51] Int. Cl.$^5$ ............................................. A61K 37/22
[52] U.S. Cl. ................................. 424/450; 264/4.1; 264/4.3; 424/88; 424/91; 436/829
[58] Field of Search .................. 424/450, 88, 91; 264/4.1, 4.3; 436/829

[56] References Cited

U.S. PATENT DOCUMENTS

| | | | |
|---|---|---|---|
| 4,164,558 | 8/1979 | von Schulthess et al. | 436/531 X |
| 4,578,270 | 3/1986 | Csizer et al. | 424/92 |
| 4,590,170 | 5/1986 | Akiyoshi et al. | 436/829 X |
| 4,619,794 | 10/1986 | Hauser | 264/4.1 |
| 4,762,720 | 8/1988 | Jizomoto | 424/450 |
| 4,944,948 | 7/1990 | Uster et al. | 424/450 |
| 5,013,555 | 5/1991 | Collins | 424/450 |
| 5,047,245 | 9/1991 | Bally et al. | 436/829 X |
| 5,049,390 | 9/1991 | Wojdani | 424/450 |

FOREIGN PATENT DOCUMENTS

3412793-A 4/1984 Fed. Rep. of Germany .

OTHER PUBLICATIONS

Mayer et al, "Techniques For Encapsulating Bioactive Agents Into Liposomes", Chemistry And Physics Of Lipids, 40(1986): pp. 333-345.

Morrison T. M., Boyd R. N. Organic Chemistry. 3rd ED. Boston, Allyn & Bacon 1973 pp. 1137-1138; 1151-1152.

*Primary Examiner*—Thurman K. Page
*Assistant Examiner*—Robert H. Harrison
*Attorney, Agent, or Firm*—Larson and Taylor

[57] ABSTRACT

In the method for combining with liposomes heterogeneous substances contained in a mixture, in particular, allergenic substances such as allergens and/or allergenic extracts, contained in an allergenic preparation, by adsorption on the surface of, and/or incorporation in, liposomes which comprise cholesterol, a phospholipid and/or at least one ionic lipid which gives the liposome a positive or negative charge, the liposome or its constituents are combined with the mixture of heterogeneous substances, the pH of the entire combination being higher or lower than the isoelectric point ip of the substances contained in the mixture, depending on whether the ionic lipid is charged positively or negatively respectively.

15 Claims, No Drawings

METHOD FOR COMBINING A MIXTURE OF HETEROGENEOUS SUBSTANCES WITH LIPOSOMES

This application is a continuation of application Ser. No. 556,727 filed Jul. 25, 1990 (now abandoned).

The invention concerns a method for combining with liposomes heterogeneous substances contained in a mixture, namely, protides or nucleic acids (or their derivatives nucleosides, nucleotides) and, in particular, allergenic substances present in an allergenic preparation, by adsorption on the surface of, and/or incorporation (encapsulation) in the liposomes, in order to produce immunization compositions, in particular, desensitizing compositions for allergic patients, or even bioreactives.

By allergenic preparations, we mean in particular preparations comprising allergens and/or various allergenic extracts, for example, pollens, acarids, phaneros or extracts thereof, or even any other animal or vegetable substances or allergenic proteins.

Liposomes are vesicles formed by one or more double layers of phospholipids and one or more aqueous compartments. Thus, they are unilamellar or multilamellar.

Liposomes have a certain number of advantages in the field of therapeutic applications:

They are not or only slightly toxic because they can be made up of natural lipids.

When they are administered subcutaneously, they promote draining of the active constituent toward the lymphatic system. This is doubly advantageous because, by going this way, the liposomes are not in contact with the represented plasma elements. Moreover, they quickly encounter the elements of the immune system since these are primarily located in the lymphatic circulation.

Use of multilamellar liposomes allows one to easily obtain an extended release system in vivo, consequently a delayed effect, which is important in the field in question. By multiplying the number of double layers, consequently the number of aqueous compartments, the duration of the action is increased.

Numerous studies using liposomes as immunological adjuvants in vaccines have been conducted (diphtheric toxin, tetanus toxin, cholera toxin, snake venom, rabies glycoprotein, adenovirus, hepatitis, subunits of influenza virus, plasmodium yoeli).

Liposomes containing allergens have also already been produced:

G. A. Stewart and A. S. McWilliam (Immune Responses to Liposome Entrapped Mite Allergens—Mite Allergy, A World-Wide Problem, September 1987, The U.C.B. Institute of Allergy) incorporated acarid allergens in three types of liposomes, unilamellar liposomes ("SUV" for "small unilamellar vesicles"), multilamellar liposomes ("MLV" for "multilamellar vesicles"), liposomes obtained by a method including an evaporation stage of the liposome solvent with allergens ("REV" for "reverse evaporation phase vesicles"). They showed that liposomes had different affinities vis-à-vis allergens.

G. Jederström (Resume of a Licentiate Thesis from the Faculty of Pharmacy, Uppsala University—Pharmaceutical Research and Development, Pharmacia AB, Box 181, S-751 82 UPPSALA, Sweden) showed the immunological activity in vivo of liposomes containing pollen.

A. S. McWILLIAM and G. A. STEWART (Journal of Immunological Methods, 121, (1989), 53–60) described liposomes ("MLV", "SUV" and "REV") containing an allergenic extract of acarids (Dermatophagoides pteronyssinus) with a view to an immunotherapy. The preparation technique of multilamellar liposomes passes through a heating phase at 50° C. for 20 minutes, which seems quite high and risks denaturizing the allergenic extract. One of the preparations using the "MLV" allowed incorporating, but with a low efficiency, the spectrum of allergens of the extract studied. The research for increasing the efficiency was conducted with solutions excluding the incorporation of certain constituents of the extract.

Liposomes are generally comprised of phospholipids and cholesterol. To increase the efficiency of encapsulation, one can combine it with a positively ($+$) or negatively ($-$) charged ionic lipid, depending on the allergen in question. This encapsulation improvement results both from an increase in the volume of aqueous compartments by repulsion of the charges between double layers and by attraction between the ionic lipid and allergen of the opposite charge.

One can then incorporate individually, with the liposome, a large variety of water-soluble compounds, the liposomes having a more or less large affinity depending on the allergen in question.

On the other hand, the combination, with liposomes, of mixtures of diverse substances, having in particular different physics-chemical characteristics, and, in particular, allergens, has not allowed one to obtain, with an acceptable efficiency, a homogeneous adsorption or encapsulation of the various constituents of the mixture. Now, in allergology in particular, one often finds mixtures containing a large range of allergenic substances with which one is not always precisely familiar, a range whose profile one must, at least, reconstruct in a delayed desensitizing composition.

It is, therefore, the object of the invention to provide a method for combining, with positively ($+$) or negatively ($-$) charged liposomes, heterogeneous substances contained in a mixture, by adsorption on the surface of, and/or incorporation in, the liposomes, which permit the fixation in large quantities of any substance according to the invention contained in the mixture while more or less maintaining the initial distribution profile of said mixture.

Another object of the invention is to provide a method which applies to all types of liposome compositions (namely, "MLV", "SUV", "REV").

Still another object of the invention is to provide a method of the type which is easy and quick to implement.

Another object of the invention is to provide delayed-action compositions in vivo, which have qualities equivalent to those of the mixtures of original substances.

The object of the present invention is a method of the type described at the beginning in which liposomes are made up of cholesterol, a phospholipid and/or at least one ionic lipid which gives the liposome a positive or negative charge. This method is characterized in that the liposome or its constituents are combined with the mixtures of heterogeneous substances, the pH of the whole being higher or lower than the isoelectric point ip of the substances contained in the mixture, depending on whether the ionic lipid is positively or negatively charged respectively.

The choice of the + or − charge given to the liposome depends, in particular, on an essential criteria, namely, that the substances must be able to support a pH alkaline or a pH acid, depending on the situation.

If the mixture is combined with liposome constituents, an adsorption of substances on the surface of the liposomes is attained as well as an incorporation of the substances therein.

If the mixture is combined with liposomes which are already formed, a simple adsorption of the substances on the liposome surface is obtained.

In the first case, one could, in a conventional manner, play in particular on the number of double layers or on the liposome composition to increase the delayed action of the composition which would thereby result.

Advantageously, the pH of the entire composition formed by the liposomes, or their constituents, and the mixture of heterogeneous substances is higher or lower than the ip of the substance whose ip is the strongest or weakest, respectively.

The ionic lipid can, in particular, be stearylamine or SA (+ charged) or dicetylphosphate or DCP (− charged).

The phospholipid can, in particular, be phosphatidyl choline of soya (PCS) or dipalmitoyl phosphatidyl choline (DPPC).

In a particular embodiment of the invention, the ionic lipid can even be a charged phospholipid, such as phosphatidyl serine in particular.

The formation of liposomes, in the pH conditions according to the invention, can in particular be carried out according to known methods which lead to the three types of liposomes cited above (G. A. Stewart et al, noted above):

Mix the aqueous solution containing the heterogeneous substances with the liposome constituents (contained in an organic solvent), then sonicate. Eliminate the organic solvents. The "REV" liposomes are obtained by evaporating the solvent with the heterogeneous substances.

Dissolve the liposome constituents in a volatile solvent, evaporate in a rotary evaporator; the constituents then form a film in contact with the wall of the evaporator; add the aqueous solution of heterogeneous substances to recover the film. The basis of this is Bangham's method (BURI P., PUISIEUX F., DOELKER F., BENOIT J. P., Vecteurs micro et nanoparticulaires. Formes pharmaceutiques nouvelles. Aspects technologiques, biopharmaceutique et médical. Ed. Lavoisier, Tec et Doc, 1985, 463-575). "MLV" multilamellar liposomes are obtained.

During agitation, slowly add the lipid constituents (in solution in a solvent) to the solution of heterogeneous substances. "SUV" unilamellar liposomes are obtained.

Of course, in the case where the method according to the invention consists in combining the mixture of heterogeneous substances and liposomes which are already formed, the solution of heterogeneous substances is replaced in the above steps by distilled water or a tampon in order to obtain "white" liposomes.

Another object of the invention are compositions obtained with the method according to the invention from allergenic preparations for desensitizing allergic patients.

Another object of the invention are compositions obtained with said method for forming bioreactives in vitro in the fields of immunology or allergology in particular. For example, this could be liposomes containing, in addition, which is already known, a detector, namely, a colored indicator. One can also envisage agglutination reactions or even use of enzymes.

An example of an allergenic composition with "MLV" liposome, for desensitizing or for forming bioreactives, is the following:

| | |
|---|---|
| phosphatidyl choline of soya | 200 mg |
| cholesterol | 30 mg |
| dicetyl phosphate | 10 mg |
| α-tocopherol | 10 mg |
| tampon or physiological phenol diluent qsp 10 ml proportioned allergenic preparation. | |

A further object of the invention are compositions obtained with said method from immunological molecules, namely, peptide sequences or immunological nucleotides to make up vaccines (hepatitis, influenza, polio, etc.)

The applicant has, moreover, discovered that it was possible to freeze-dry the compositions in which heterogeneous substances are incorporated without adding cryoprotective agents. The presence of said heterogeneous substances will be sufficient to stabilize the liposomes.

In the case where only the heterogeneous substances are adsorbed, it can be useful to add, in a conventional manner, a cryoprotective agent.

Thus, compositions of the above type which have been freeze-dried with or without a cryoprotective agent are an object of the invention.

The invention shall now be described in greater detail with reference to an example, but not restricted thereto, concerning the combination of allergenic substances according to the invention with "MLV"-type multilamellar liposomes.

The constituents of the liposomes used in this example are the following:

1. for the phospholipids:

phosphatidyl choline of soya, PCS, épikuron 200, molecular weight 780 (Lucas Meyer France SA, Saint Maur Les Fossés), dipalmitoyl phosphatidyl choline, DPPC, molecular weight 734 (Sigma SARL, La Verpillère, France).

2. for ionic lipids:

stearylamine, SA, which brings a positive charge to the liposomes (Sigma Chimie SARL), molecular weight=269.5, dicetylphosphate, DCP, which brings a negative charge (Sigma Chimie SARL); molecular weight=549.9

3. cholesterol, CH (Sigma Chimie SARL)

4. possibly an antioxidant, for example, α-tocopherol, αT, to prevent the oxidation of the phospholipid.

The preparation of the liposomes can be carried out by Bangham's method which has already been noted:

Dissolving the lipids in the chloroform at a concentration of 20 mg of phospholipids per milliliter.

Evaporation in a vacuum in a rotary evaporator at 35° C. for PCS-based liposomes, and at 50° C. for DPPC-based liposomes. A film forms on the walls.

Recovery of the film by an aqueous solution, at a temperature higher than the transition temperature of the lipid mixture phase. In the case of the PCS, one works at room temperature, in the case of the DPPC, at 40° C.

By simple agitation, the lipids work loose from the wall of the evaporator balloon and form a milky suspension of multilamellar liposomes. The phospholipids spontaneously assume the double-layer structure when they are dispersed in an excess of water. The liposome suspension obtained is left to swell at 4° C.

The allergens can be incorporated in two ways:

Recovery of the above film by the allergenic solution as an aqueous solution. These are going to be recovered between the double layers and on the liposome surface. This is the method described by Bangham. Type-B liposomes result.

Recovery of the film by a tampon or by distilled water. White liposomes are then obtained. In a second step, one proceeds to mix these liposomes with an allergenic solution. These will only be found on the surface of the liposomes and these liposomes are called type-A liposomes.

In an advantageous embodiment, the method according to the invention, applied to positively charged liposomes (containing SA), consists in giving the aqueous solution of allergens, with the help of HCl O, 1N, a pH so that, after combining with said solution and the liposomes or their constituents, depending on the case, the resultant mixture finally has a pH which is higher than the ip of the allergen (the allergens generally have an ip which is between about 4 and about 6) whose ip is the strongest.

In the case of negatively charged liposomes (containing DCP), the resultant mixture must have a pH which is lower than the ip of the allergen whose ip is the weakest.

One can, of course, consider other ways of bringing the pH of the mixture to the desired value. One can, for example, adjust the pH after combining the allergens and liposomes or their constituents.

The next example relates to the following allergens:
pollens (five Graminaceae)
acarids (Dermatophagoides pteronyssinus or DPtero, and Dermatophagoides farinas)
phaneros (cat hair and dog hair)
a pollen extract of one gramineous plant, the dactyl (this is, in fact, a mixture of several proteins, giving 20 bands to electrofocusing).

The formula retained for preparing the liposomes is the following: PCS/Ch/SA or DCP/$\alpha$T ionic lipid, for a molar ratio of 7/2/0.5/1.

In a first step, the allergens are fixed to the liposomes by simply following Bangham's method.

The results (incorporation efficiency) obtained are summarized in Table I which follows. This relates to type-B liposomes.

TABLE I

|  | PCS/Ch/SA | PCS/Ch/DCP |
|---|---|---|
| Pollens | 10 to 20% | 50% |
| Acarids | 10 to 15% | 60% |
| Phaneros | 50 to 60% | 10 to 20% |

This table shows the affinity differences of liposomes vis-à-vis the different allergens.

The method according to the invention was then applied to constructing type-B liposomes containing cat hair allergens.

Table II, which follows, combines the results obtained in the case where the pH of the liposome-allergen mixture is higher than the isoelectric point (ip) of the allergens (which is often the case when following Bangham's method) and in the case where the pH is reduced, for example, with a solution of HCl O, 1N, to a final value lower than the ip of the allergens, the ionic lipid used being DCP (negative charge).

TABLE II

|  |  | pH | IR |
|---|---|---|---|
| Allergen solution |  | 7.64 | 54 |
| White liposomes with DCP |  | 3.17 | 0 |
| Liposomes with DCP + allergen solution to pH 7.64 (2 tests) | 1. | 7.59 | 5.5 |
|  | 2. | 7.81 | 3.5 |
| Liposomes with DCP + allergen solution to pH 3.92 (2 tests) | 1. | 3.57 | 44 |
|  | 2. | 3.55 | 43 |

IR: internal reactivity factor.

This factor is obtained by radio-immunological dose, by the RAST-inhibition (Radio Allergo Sorbent Test) method which measures the immunological activity of allergens.

The skin reactivity factor 100 IR is defined in vivo by a population of 30 allergen-sensitive subjects in such a way that, after scarification by injection on the inside of the forearm, the average surface of the papule produced was 30 mm$^2$, that is a diameter of about 6 mm.

In the case of allergens encapsuled in the liposomes, it is first of all necessary to separate the allergens from their support. To accomplish this, the method proposed by JULIANO R. L. and LIN G. is used. (The Interaction of Plasma Proteins with Liposomes: Protein Binding and Effects on the Dotting and Complement Systems—Liposomes and Immunology, 1980, Tom I Six by Elsevier). They use ethanol to make the lipids making up the liposomes soluble and to isolate the proteins by precipitation.

The liposomes are separated, then:
the residual floating activity is determined by RAST-inhibition;
the liposome base is contacted with 9 volumes of absolute ethanol for 1 hour at 0° C., 15 mm is centrifuged at 5000 tr/mn, the protein base obtained is recovered and dissolved in PBS; the activity is then determined by RAST-inhibition.

Table II above shows the effectiveness of the method according to the invention. By placing at a pH ip in the case of a negatively charged liposome, an adsorption efficiency and allergen incorporation of cat hair greater than 50% is obtained.

Equivalent results were obtained with Dactyl and DPtero allergens.

Freeze-drying the allergens does not pose a particular problem since it is actually used to assure conservation of the allergenic extracts.

Freeze-drying the liposomes combined with the allergens must meet the following criteria:
keeping the structural entirety of the liposomes,
constant rate of adsorption and incorporation of allergens,
easy dispersion of the freeze-dried liposomes after recovery from freeze-drying by an appropriate aqueous phase.

The conditions for freeze-drying are freezing at 30° C., then a sublimation for 20 hours. An Alpha I-5 freeze-drier was used (Bioblock Scientific, Paris).

All the criteria were respected, no matter what the liposome composition was.

The applicant has discovered that the encapsuled allergens probably play the role of cryoprotector.

We are now going to give an example of an allergenic composition according to the invention for MLV-type liposomes:

| | |
|---|---|
| phosphatidyl choline of soya | 200 mg |
| cholesterol | 30 mg |
| dicetylphosphate | 10 mg |
| α-tocopherol | 10 mg |
| qsp solution 10 ml | |
| Dactyl extract dosed in I.R. | |

As a solution, one can use any physiological phenol diluent as well as any physiological phenol tampon.

This composition can be used to desensitize allergic patients or to form bioreactives.

We claim:

1. A method of combining protidic allergens and/or allergenic extracts selected from the group consisting of natural allergens from animal or vegetable origin, allergenic proteins and peptides, with a negatively or positively charged liposome comprised of cholesterol, a phospholipid and/or at least one ionic lipid which gives the liposome a positive or negative charge, comprising a) determining the isoelectric point ip of one or more of the allergenic substances to be mixed and b) mixing said allergenic substance or substances with said liposome at a pH lower than said isoelectric point when the liposome is negatively charged or at a pH higher than said isoelectric point when said liposome is positively charged.

2. A method according to claim 1 wherein the liposome is positively charged and the weakest isoelectric point of said substance is determined.

3. A method according to claim 1 wherein the liposome is negatively charged and the strongest isoelectric point of said substance is determined.

4. Method according to claim 1, wherein before step b), one adjusts the pH of the mixture of heterogeneous substances at such a value that the pH of step b) will be subsequently obtained.

5. Method according to claim 1, wherein the ionic lipid is a stearylamine.

6. Method according to claim 1, wherein the ionic lipid is a dicetylphosphate.

7. Method according to claim 1, wherein the phospholipid is a phosphatidyl choline of soya or a dipalmitoyl phosphatidyl choline.

8. Method according to claim 1, wherein the ionic lipid is a phospholipid.

9. Method according to claim 7, wherein the phospholipid is a phosphatidyl serine.

10. Method according to claim 1, wherein the liposome is a multilamellar vesicle.

11. Method according to claim 1, wherein the liposome is a small unilamellar vesicle.

12. Method according to claim 1, wherein the liposome is a reverse evaporation phase vesicle.

13. The product obtained by the method according to claim 1.

14. The product obtained by the method of claim 12.

15. A product obtained by the method of claim 12 in freeze-dried form.

* * * * *